(12) United States Patent
Ponyavin et al.

(10) Patent No.: US 11,873,764 B2
(45) Date of Patent: Jan. 16, 2024

(54) HAZARDOUS GAS MONITORING SYSTEM

(71) Applicant: GENERAL ELECTRIC COMPANY, Schenectady, NY (US)

(72) Inventors: Valery Ivanovich Ponyavin, Greenville, SC (US); Melinda Stephanie Ammerman, Simpsonville, SC (US); Miguel Angel Mendoza, Queretaro (MX); Jaymil Jitendrakumar Patel, Lexington, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 362 days.

(21) Appl. No.: 16/892,469

(22) Filed: Jun. 4, 2020

(65) Prior Publication Data
US 2021/0381437 A1 Dec. 9, 2021

(51) Int. Cl.
| | |
|---|---|
| *F02C 7/25* | (2006.01) |
| *C10K 1/00* | (2006.01) |
| *F02C 3/22* | (2006.01) |
| *G01N 1/26* | (2006.01) |
| *G01N 21/3504* | (2014.01) |
| *G01N 33/00* | (2006.01) |

(52) U.S. Cl.
CPC ............... *F02C 7/25* (2013.01); *C10K 1/002* (2013.01); *F02C 3/22* (2013.01); *G01N 1/26* (2013.01); *G01N 21/3504* (2013.01); *G01N 33/0011* (2013.01); *G01N 33/0036* (2013.01)

(58) Field of Classification Search
CPC .. F02C 7/25; F02C 3/22; C10K 1/002; G01N 1/26; G01N 21/3504; G01N 33/0036; G01N 33/0011
See application file for complete search history.

(56) References Cited

U.S. PATENT DOCUMENTS

| | | | | |
|---|---|---|---|---|
| 5,918,616 A | * | 7/1999 | Sanfilippo | F16K 27/003 137/884 |
| 6,167,766 B1 | * | 1/2001 | Dunn | G01N 1/18 73/863.01 |
| 9,366,192 B2 | | 6/2016 | Byrd et al. | |

(Continued)

FOREIGN PATENT DOCUMENTS

| | | | | |
|---|---|---|---|---|
| CN | 108872124 A | * | 11/2018 | ............. F27B 17/02 |
| GB | 190112923 A | * | 6/1901 | |
| JP | 5885015 B2 | * | 3/2016 | |

OTHER PUBLICATIONS

Machine Translation of CN 108872124 A (Year: 2018).*
Machine Translation of JP 5885015 B2 (Year: 2016).*

*Primary Examiner* — Nathaniel J Kolb
(74) *Attorney, Agent, or Firm* — Fletcher Yoder, P.C.

(57) ABSTRACT

A hazardous gas monitoring system is provided. The hazardous gas monitoring system includes a panel including multiple sensing lines. Each sensing line is configured to receive and monitor an air sample. Each sensing line includes a water separator to remove condensed moisture, a coalescing filter disposed downstream of the water separator, and a flow and gas monitoring system disposed downstream of the coalescing filter. The hazardous gas monitoring system may be used to monitor the presence of hazardous gases within an enclosure, such as an enclosure for a turbomachine.

19 Claims, 5 Drawing Sheets

(56) References Cited

U.S. PATENT DOCUMENTS

| | | | | |
|---|---|---|---|---|
| 2004/0099045 A1* | 5/2004 | Demarest | ................ | C25B 15/08 |
| | | | | 73/23.2 |
| 2008/0029389 A1* | 2/2008 | Dreier | .................... | C25B 15/00 |
| | | | | 205/637 |
| 2011/0313670 A1* | 12/2011 | DeGreeve | ............... | E21B 49/00 |
| | | | | 356/51 |
| 2015/0226129 A1* | 8/2015 | Byrd | ................... | G01M 15/102 |
| | | | | 73/23.31 |
| 2018/0238797 A1* | 8/2018 | Sanroma | ........... | G01N 33/0016 |

* cited by examiner

HAZARDOUS GAS MONITORING SYSTEM

BACKGROUND

The present disclosure relates generally to turbomachines. In particular, the present disclosure relates to systems for hazardous gas monitoring in an enclosure of a turbomachine.

Gas turbines and/or generators (e.g., hydrogen-cooled generators) are used to generate power for various applications. To protect the turbine and/or generator from the surrounding environment and vise versa, the turbine and/or generator may be housed or enclosed in an enclosure with appropriate inlets, exhaust outlets, and/or ventilations, etc. For example, a gas turbine and/or generator may be housed inside an enclosure, which may facilitate reducing noise during turbine operation and which may contain environmental hazards such as combustible gases (e.g., fuel gas or hydrogen) from leaking to the surrounding environment. A monitoring system may be fluidly coupled to an enclosure to sample the air within the enclosure to detect the presence of hazardous gas. Unfortunately, under certain conditions, these monitoring systems may trip the power generation units (e.g., due to moisture or ice in the sensing lines), resulting in unnecessary costly shutdowns. Due to this issue, certain operators may inactivate monitoring systems and forego monitoring for hazardous gas within the enclosure.

BRIEF DESCRIPTION

Certain embodiments commensurate in scope with the originally claimed subject matter are summarized below. These embodiments are not intended to limit the scope of the claimed embodiments, but rather these embodiments are intended only to provide a brief summary of possible forms of the subject matter. Indeed, the presently claimed embodiments may encompass a variety of forms that may be similar to or different from the embodiments set forth below.

In a first embodiment, a hazardous gas monitoring system is provided. The hazardous gas monitoring system includes a panel including multiple sensing lines. Each sensing line is configured to receive and monitor an air sample. Each sensing line includes a water separator to remove condensed moisture, a coalescing filter disposed downstream of the water separator, and a flow and gas monitoring system disposed downstream of the coalescing filter.

In a second embodiment, a hazardous gas monitoring system is provided. The hazardous gas monitoring system includes a panel including multiple sensing lines. Each sensing line is configured to receive and monitor an air sample from an enclosure housing a turbomachine. Each sensing line includes a water separator to remove condensed moisture, and the multiple sensing lines discharge respective air samples to the atmosphere.

In a third embodiment, a hazardous gas monitoring system is provided. The hazardous gas monitoring system includes a panel including a first sensing line and a second sensing line. The first and second sensing lines are each configured to receive and monitor an air sample from an enclosure housing a turbomachine. The first and second sensing lines each include a water separator to remove condensed moisture. Respective water separators of the first and second sensing lines are coupled to a common drainage line, and a respective orifice is disposed between each respective water separator and the common drainage line.

BRIEF DESCRIPTION OF THE DRAWINGS

These and other features, aspects, and advantages of the presently disclosed techniques will become better understood when the following detailed description is read with reference to the accompanying drawings in which like characters represent like parts throughout the drawings, wherein.

DETAILED DESCRIPTION

Figure 1:
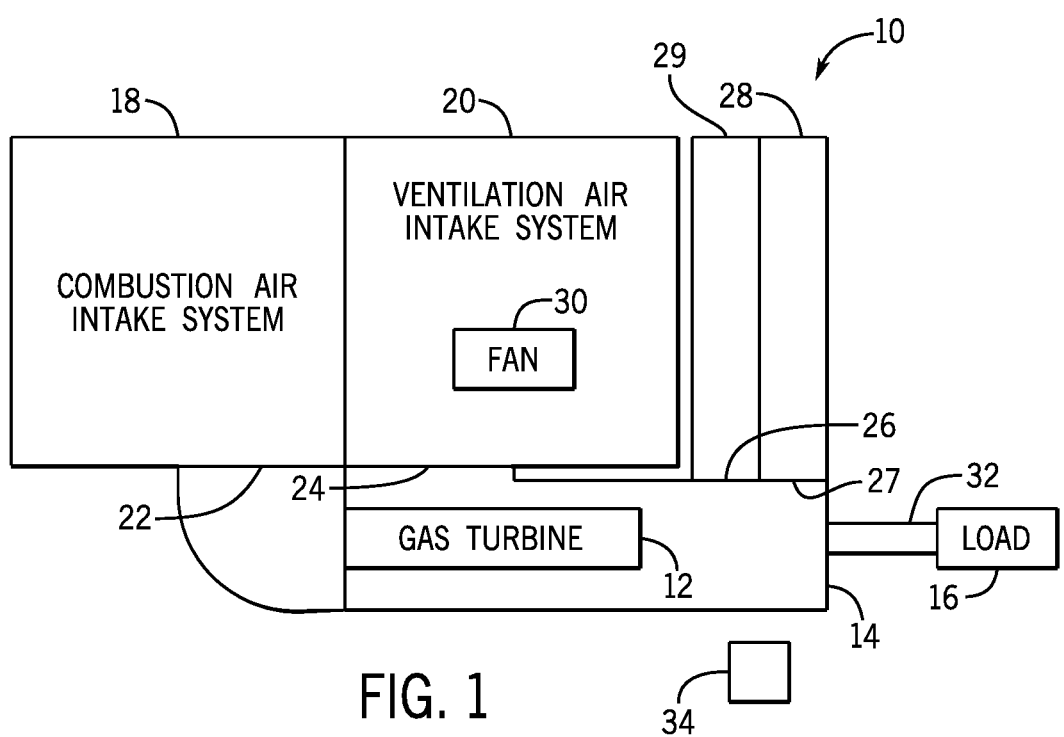
FIG. 1 is a partial schematic illustration of a turbine system having a gas turbine in a gas turbine enclosure utilizing a hazardous gas monitoring system for monitoring for gas leakage, in accordance with an embodiment.

One or more specific embodiments of the presently disclosed embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the presently disclosed embodiments, the articles "a," "an," "the," and "said" are intended to mean that there are one or more of the elements. The terms "comprising," "including," and "having" are intended to be inclusive and mean that there may be additional elements other than the listed elements.

As described below, a hazardous gas monitoring system is intended for monitoring presence of hazardous gases (e.g., combustible gases, such as a fuel gas (e.g., natural gas) in a gas turbine enclosure or hydrogen in a generator enclosure) inside an equipment area (e.g., an enclosure) for a turbomachine (e.g., a gas turbine, a generator, etc.). In particular, the hazardous gas monitoring system includes a panel with freezing and moisture buildup protection. The panel includes multiple sensing lines or sensing conduits that provide air samples from sensing points (where sample probes are located) in one or more enclosures. Each sensing line includes a flow monitor configured to proactively monitor and determine if the sample flow drops to an unacceptable level.

Each sensing line also includes a water separator to remove condensed moisture from the sensing lines to reduce the likelihood of freezing. To keep any remaining condensed water from freezing within the sensing lines, the panel may be disposed within a cabinet with a heater and a thermostat. In addition, the portions of the sensing lines disposed outside of the panel may have heat traces on them to keep water from freezing within the sensing lines. By keeping moisture from building up or freezing from occurring in the monitoring system, the reliability of the monitoring system may be increased, while avoiding costly and unnecessary shutdowns or trips of the power generation system.

In certain embodiments, at least one sensing line may be inactive (e.g., for a sensor change out or maintenance) while another sensing line is still active to enable the turbomachine to keep operating. Further, in some embodiments, the sensing lines may discharge the air samples after monitoring to the atmosphere (instead of returning them to the enclosure via an exhaust line) to avoid back pressure that may impact the monitoring system.

FIG. 1 is a partial schematic of an embodiment of a turbine system 10, enclosed or housed by a turbine enclosure 14 (e.g., gas turbine enclosure). The turbine system 10 may be a stationary or mobile gas turbine power generation unit. For example, the turbine system 10 may be a stationary unit disposed in a power plant, such as integrated gasification combined cycle (IGCC) power plant. For example, the turbine system 10 may be a mobile unit carried by a trailer. The turbine system 10 includes a gas turbine or gas turbine engine 12, the enclosure 14 (e.g., gas turbine enclosure) that houses the gas turbine 12, and a load 16 (e.g., generator, electrical generator) driven by the gas turbine 12. The turbine system 10 also includes a combustion air intake system 18 upstream from the gas turbine 12 and a ventilation air intake system 20. The gas turbine enclosure 14 may define a first intake port 22 (e.g., first air intake port or turbine air intake), a second intake port 24 (e.g., second air intake port or enclosure ventilation intake), an air exit port 26, and an exhaust exit port 27.

The first intake port 22 is coupled to the combustion air intake system 18 upstream from the gas turbine 12. The combustion air intake system 18 may include one or more filters to filter air provided to the gas turbine 12. The first intake port 22 directs air into the gas turbine 12. For example, the first intake port 22 may direct air into a compressor of the gas turbine 12. For example, the gas turbine 12 may compress the air from port 22, mix the air with fuel in one or combustors, and combust the air-fuel mixture to drive one or more turbines.

The second intake port 24 is coupled to the ventilation air intake system 20. The ventilation air intake system 20 may include one or more filters to filter air provided to the enclosure 14 of the gas turbine 12. The ventilation air intake system 20 may provide air into the enclosure 14 via one or more fans 30. The second intake port 24 directs air into the enclosure 14 surrounding the gas turbine 12 to ventilate the enclosure.

The exhaust exit port 27 is coupled to a combustion exhaust stack or combustion exhaust duct 28 for venting exhaust gases from the gas turbine 12. The air exit port 26 is coupled to a duct 29 for discharging the ventilation air. The gas turbine 12 includes a shaft 32 that extends through the enclosure 14 and couples to the load 16. As described in greater detail below, a hazardous gas monitoring system 34 may be utilized to monitor for the presence of hazardous gases (e.g., combustible gases) within the enclosure 14. The hazardous gas monitoring system 34 is an aspirated system that samples air from the enclosure 14 and monitors gas concentration to determine an appropriate safety action if hazardous gas is present. As described in greater detail below, the hazardous gas monitoring system 34 is configured to keep moisture from accumulating or freezing in the monitoring system 34.

Figure 2:
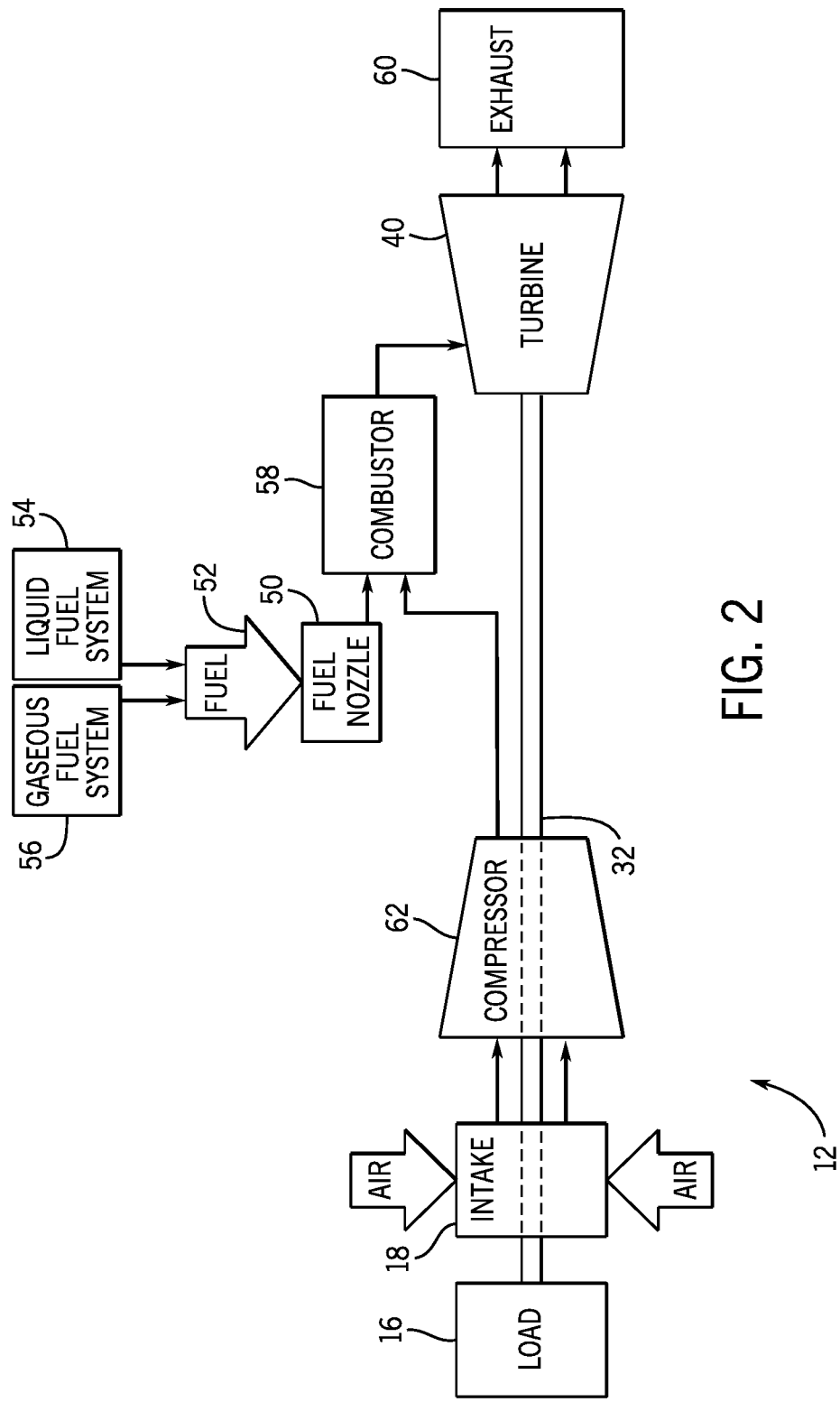
FIG. 2 is a schematic illustration of the turbine system utilizing the hazardous gas monitoring system for monitoring for gas leakage, in accordance with an embodiment of the present disclosure.

FIG. 2 is a schematic of an embodiment of the turbine system 10 utilizing the present hazardous gas monitoring system 34 for monitoring for gas leakage. The turbine system (e.g., gas turbine system, dual-fuel turbine system) 10 may use liquid or gas fuel, such as natural gas and/or a hydrogen rich synthetic gas, to drive the turbine system 10. As depicted, in each combustor 58 of a plurality of combustors 58, fuel nozzles 50 (e.g., multi-tube fuel nozzles) intake a fuel supply 52 from a liquid fuel system 54 or a gaseous fuel system 56 and mix the fuel with an oxidant (such as air, oxygen, oxygen-enriched air, oxygen reduced air, or any combination thereof), which may be supplied by a compressor 62. Although the following discussion refers to the oxidant as the air, any suitable oxidant may be used with the disclosed embodiments.

Once the fuel and air have been mixed, the fuel nozzles 50 distribute the fuel-air mixture in a suitable ratio for optimal combustion, emissions, fuel consumption, and power output. The turbine system 10 may include one or more fuel nozzles 50 located inside each of the plurality of combustors 58. The fuel-air mixture combusts in a chamber within each of the plurality of combustors 58, thereby creating hot pressurized exhaust gases.

The plurality of combustors 58 direct the exhaust gases through a turbine section (or "expansion turbine") 40 of the gas turbine 12 toward an exhaust outlet 60 (e.g., directed to the exit port 27). As the exhaust gases pass through the turbine section 40, the gases force turbine blades to rotate the drive shaft 32 along an axis of the turbine system 10. As illustrated, the shaft 32 may be connected to various components of the turbine system 10, including the compressor 62. The compressor 62 also includes blades coupled to the shaft 32. As the shaft 32 rotates, the blades within the compressor 62 also rotate, thereby compressing air from the first (air) intake port 22 through the compressor 62 and into the fuel nozzles 50 and/or the plurality of combustors 58. The fuel nozzles 50 may contain fuel plenums or may connect with an end cover having fuel plenums, which may improve fuel distribution within the nozzles 50 before the fuel-air mixture is discharged into the combustor 58.

The shaft 32 may also be connected to the load 16, which may be a vehicle or a stationary load, such as an electrical generator in a power plant or a propeller on an aircraft, for example. The load 16 may include any suitable device capable of being powered by the rotational output of the turbine system 10.

As described in greater detail below, the hazardous gas monitoring system 34 may be utilized to sample air within the enclosure 14 for detecting, monitoring, and assessing the presence and volume of hazardous gases, which may be present in the event of a fuel leak. Although the hazardous gas monitoring system 34 has been discussed relative to a gas turbine system 10, the monitoring system 34 may be utilized with other turbomachines, such as hydrogen-cooled generators. In addition, the hazardous gas monitoring system 34 may be utilized to monitor any other type of equipment area or enclosure where it is desirable to monitor for the presence of hazardous gases.

Figure 3:
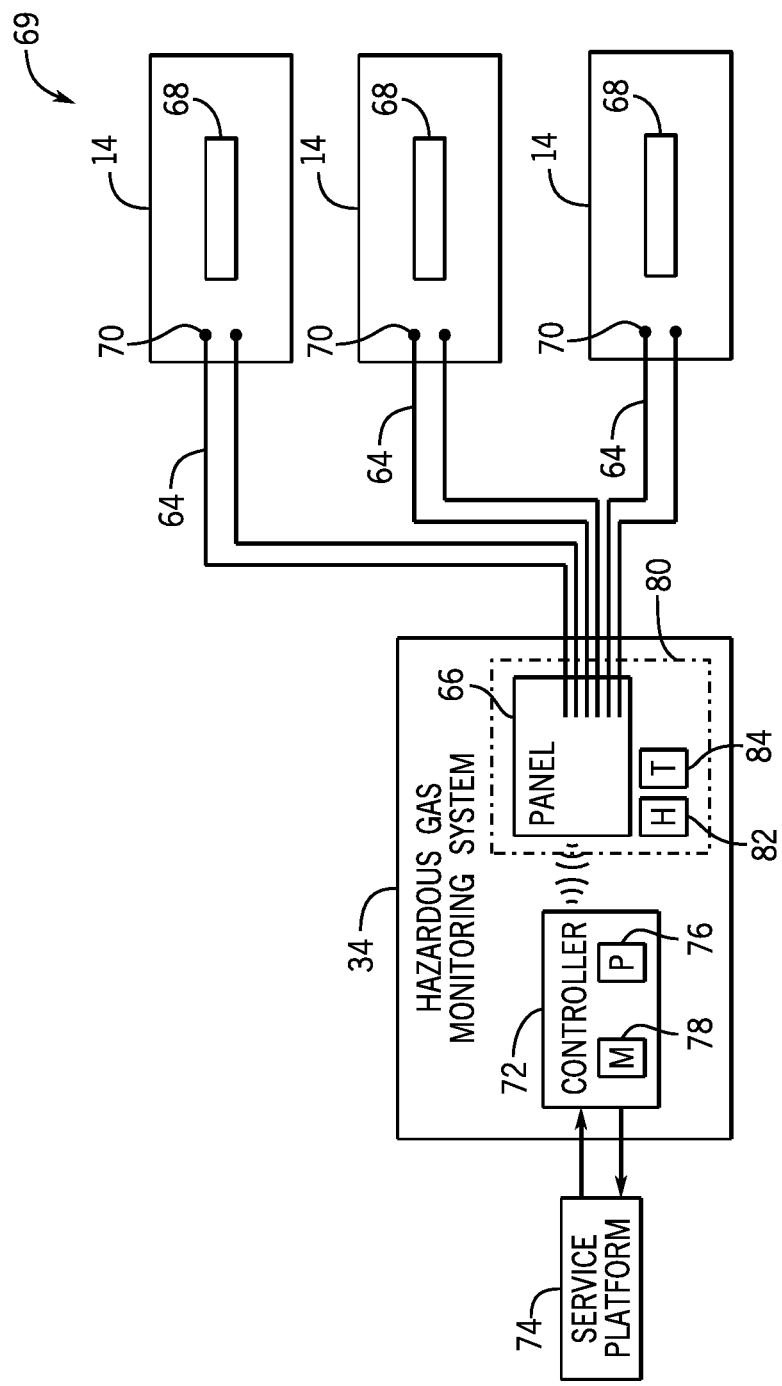
FIG. 3 is a schematic illustration of an embodiment of a hazardous gas monitoring system coupled to a plurality of enclosures.

FIG. 3 is a schematic illustration of the present hazardous gas monitoring system 34 (e.g., aspirated driven system) coupled to a plurality of enclosures 14. The hazardous gas monitoring system 34 includes a plurality of sensing lines 64 coupled to the enclosures 14. The number of enclosures 14 coupled to the hazardous gas monitoring system 34 (in particular, a panel 66 of the system 34) may vary (e.g., 1, 2, 3, 4, or more). Each enclosure 14 includes a turbomachine 68 (e.g., gas turbine 12, generator, or other turbomachine).

The turbomachines 68 may form a portion of a power plant 69. One or more sensing lines 64 may be coupled to each enclosure 14. As depicted, at least two sensing lines 64 are coupled to each enclosure 14. Each sensing line 64 extends into the respective enclosure 14 to a sensing point 70 where an air sample is aspirated into the sensing line 64. In certain embodiments, the panel 66 may be disposed within a cabinet 80. The cabinet 80 may include a heater 82 to keep the sensing lines 64 coupled to the panel 66 above freezing (0 degrees Celsius) to keep any moisture within the sensing lines 64 from freezing. The cabinet 80 may also include a thermostat 84 to provide an indication of the temperature within the cabinet 80.

The hazardous gas monitoring system 34 includes a controller 72 communicatively coupled to a flow and gas monitoring system 96 (FIG. 4) of each sensing line 64. In certain embodiments, the controller 72 is communicatively coupled (e.g., data transfer, receiving and giving instructions) with a service platform 74 (e.g., cloud computing service, distributed control system) and/or various components and systems of the turbomachines 68 via wired or wireless network or communication system. In some embodiments, the controller 72 may be part of the service platform 74. The controller 72 has a processor 76 and a memory 78 (e.g., a non-transitory computer-readable medium/memory circuitry) communicatively coupled to the processor 76, storing one or more sets of instructions (e.g., processor-executable instructions) implemented to perform operations related to the hazardous gas monitoring system 34 and/or turbomachines 68.

For example, operations may relate to monitoring the flow of the sample within each sensing line 64, regulating a temperature within the cabinet 80 via the heater 82, regulating a temperature of heat traces on portions of the sensing lines 64 outside of the panel 66 (discussed further herein), monitoring the presence of hazardous gases within the air samples, and/or providing an action (e.g., safety action such as shutting down an individual turbomachine 68 or providing a user perceptible warning) in response to detecting hazardous gas at an actionable concentration or volume.

More specifically, the memory 78 may include volatile memory, such as random-access memory (RAM), and/or non-volatile memory, such as read-only memory (ROM), optical drives, hard disc drives, or solid-state drives. Additionally, the processor 76 may include one or more application specific integrated circuits (ASICs), one or more field programmable gate arrays (FPGAs), one or more general purpose processors, or any combination thereof. Furthermore, the term "processor" is not limited to just those integrated circuits referred to in the art as processors, but broadly refers to computers, processors, microcontrollers, microcomputers, programmable logic controllers, application specific integrated circuits, and other programmable circuits.

For example, the memory 78 may store various limits or ranges related to parameters (e.g., flow rate, flow speed, flow volume, etc.) of a flow of the samples within the sampling lines 64, temperature within the cabinet 80 or on the sampling lines outside the cabinet, and/or hazardous gas concentrations (and associated upper and lower level explosive limits). For example, the memory 78 may store information inputted by operators or users (e.g., via the controller 72 and/or via the service platform 74). Information may be collected via the flow and gas monitoring system 96 (FIG. 4) of each sensing line 64, thermostat 84, or other equipment (e.g., temperature sensor providing ambient temperature about the monitoring system 34).

Figure 4:
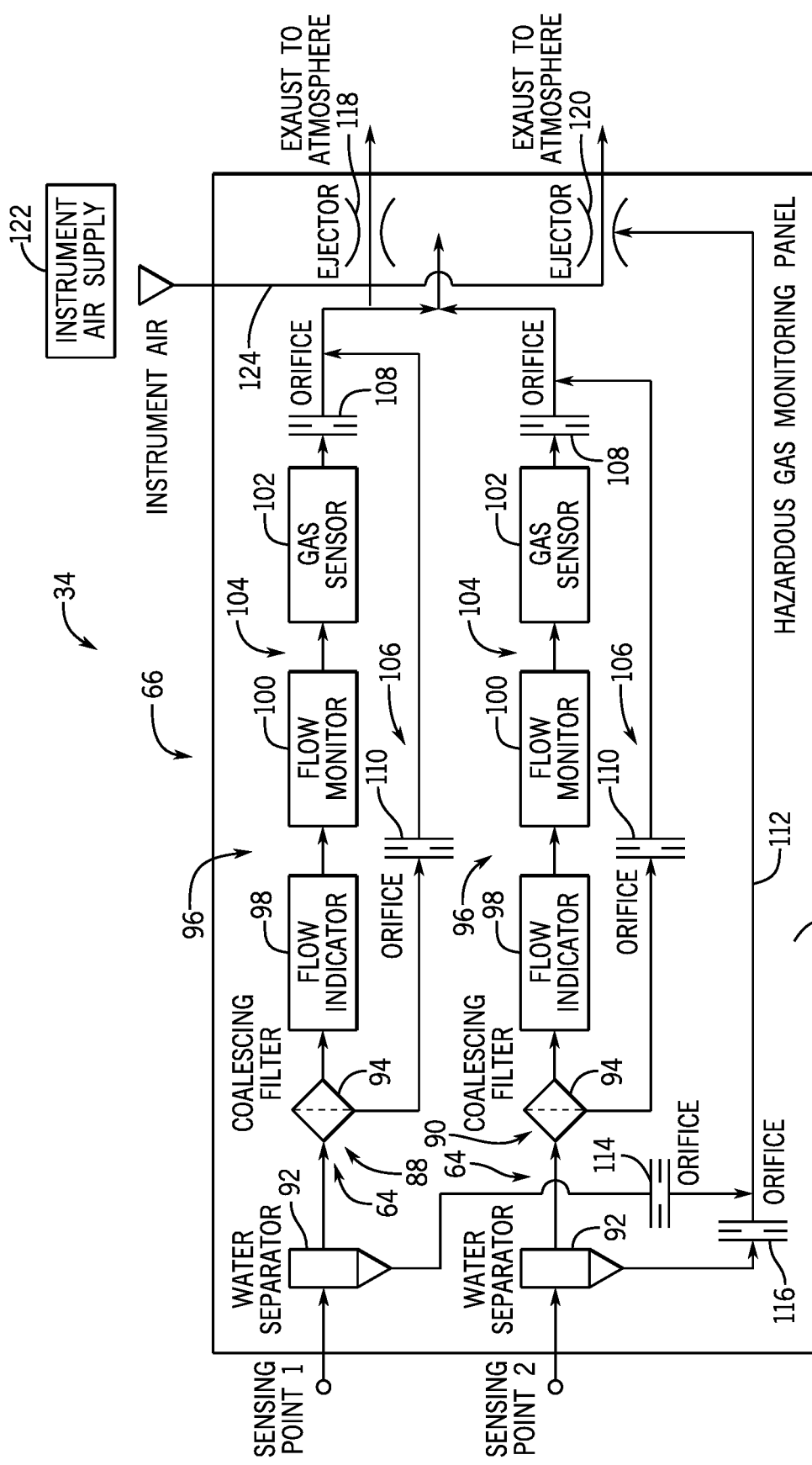
FIG. 4 is a schematic illustration of an embodiment of a panel (e.g., a hazardous gas detection panel) of a hazardous gas monitoring system.

FIG. 4 is a schematic illustration of an embodiment of the panel 66 (e.g., hazardous gas monitoring panel) of a hazardous gas monitoring system 34. The panel 66 includes a panel wall 86. The panel wall 86 includes a plurality of sensing lines 64. As depicted, the panel wall 86 includes two sensing lines 64 (e.g., sensing lines 88, 90). As noted above, the number of sensing lines 64 associated with the panel 66 may vary (e.g., 1, 2, 3, 4, or more). As depicted, the sensing lines 88, 90 are associated with sensing points 1 and 2 from which a respective air sample is aspirated. Sensing points 1 and 2 may disposed in the same enclosure (e.g., housing a turbomachine) or different enclosures. In certain embodiments, each enclosure may include two or more sensing points (and associated sensing lines 64) coupled to the panel 66.

Each sensing line 64 includes a water separator 92, a coalescing filter or coalescer 94, and a flow and gas monitoring system 96 disposed downstream of the coalescer 94. The water separator 92 removes condensed moisture from the sensing line 64. The coalescer 94 further separates moisture from the sensing line 64. The flow and gas monitoring system 96 includes a flow indicator 98, a flow monitor 100, and one or more gas sensors 102. The flow and gas monitoring system 96 may be communicatively coupled to a controller (e.g., controller 72 of FIG. 3). The flow indicator 98 (e.g., ball style sight flow indicator) provides a visual indication of sample flow in the sensing line 64. The flow monitor 100 includes one or more sensors (e.g., flow meters, ultrasonic flow meters, etc.) and circuitry (e.g., processing and memory circuitry) to detect a parameter (e.g., flow rate, flow volume, etc.) of the sample flow in a respective sensing line and to determine if the parameter is at an undesired level (e.g., outside a range, below a certain limit, etc.). The one or more gas sensors 102 are utilized to detect a presence of a hazardous gas in the sample flow. The one or more gas sensors 102 may include microstructured gas sensors, flow infrared point sensors, infrared cameras, and/or ultrasonic sensors. The one or more gas sensors 102 may be able to detect one or more specific gases (e.g., natural gas, hydrogen, etc.). As depicted in FIG. 4, the flow monitor 100 is disposed downstream of the flow indicator 98 and the one or more gas sensors 102 are disposed downstream of both the flow indicator 98 and the flow monitor 100. In certain embodiments, the flow indicator 98, the flow monitor 100, and the one or more gas sensors 102 may be disposed in a different order.

As depicted in FIG. 4, at the coalescer 94, each sensing line 64 splits into a flow and gas monitoring line 104 and a drainage line 106. The air sample to be monitored flows along the flow and gas monitoring line 104 through the flow and gas monitoring system 96, and any moisture separated from the air sample flows along the drainage line 106. An orifice 108 (e.g., flow limiting orifice) is disposed along the flow and gas monitoring line 104 downstream of the flow and gas monitoring system 96. An orifice 110 (e.g., flow limiting orifice) is also disposed along the drainage line 106. The orifices 108, 110 are sized for optimal flow split and/or pressure drop among the various lines. The flow and gas monitoring line 104 and the drainage line 106 join again downstream of the orifices 108, 110. Downstream of the merging of the respective flow and gas monitoring lines 104 and drainage lines 106 of the sensing lines 88, 90, the sensing lines 88, 90 merge for the discharge of the air samples from an ejector 118 into the atmosphere.

Moisture separated from the respective water separators 92 of the sensing lines 88, 90 flow to a common drainage line 112. Orifices 114, 116 (e.g., flow limiting orifices) are disposed between the respective water separators 92 and the common drainage line 112. The orifices 114, 116 are sized for optimal flow split and/or pressure drop between the various lines. The common drainage line 112 discharges the moisture from the air samples from a separate ejector 120.

To facilitate discharge (e.g., via aspiration) of the sample to the atmosphere from ejectors 118, 120, instrument air is provided from an instrument air supply 122, via air line 124, to each of the ejectors 118, 120. Discharging the air samples into the atmosphere (instead of returning them via an exhaust line to the enclosure) keeps back pressure from forming and hindering flow within the system.

In certain embodiments, at least one sensing line 64 (e.g., sensing line 88) may be inactive while another sensing line 64 (e.g., sensing line 90) is still active to enable the turbomachine (e.g., gas turbine or generator) to keep operating. This may enable a sensor change out or maintenance for the sensing line 88, while the other sensing line 90 monitors for the presence of hazardous gas in the enclosure.

Figure 5:
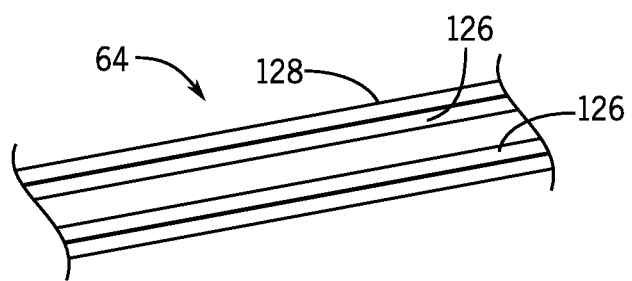
FIG. 5 is a schematic illustration of an embodiment of a sensing line with heat traces, which may be used in embodiments of the present hazardous gas monitoring system.

FIG. 5 is a schematic illustration of an embodiment of the sensing line 64 with heat traces 126. The heat traces 126 are disposed on a conduit wall 128 of the sensing line 64. The heat traces 126 may maintain or raise the temperature of the conduit wall 128 to keep the temperature of the sensing line 64 above freezing (0 degrees Celsius) to keep moisture from freezing within the sensing line 64. In certain embodiments, each heat trace 126 may take the form of an electrical heating element run in physical contact along the length of a conduit wall 128. In certain embodiments, the heat traces 126 may be controlled by a controller (e.g., controller 72 in FIG. 3).

Technical effects of the disclosed embodiments include providing a hazardous gas monitoring system that includes a panel coupled to a plurality of sensing lines, which in turn are coupled to one or more enclosures (e.g., enclosures housing turbomachines). The panel includes features to avoid moisture accumulation and freezing of moisture within the sensing lines. By keeping moisture from building up or freezing from occurring in the monitoring system, the reliability of the monitoring system may be increased, while avoiding costly and unnecessary shutdowns or trips of the power generation system.

This written description uses examples to describe the present embodiments, including the best mode, and also to enable any person skilled in the art to practice the presently disclosed embodiments, including making and using any devices or systems and performing any incorporated methods. The patentable scope of the presently disclosed embodiments is defined by the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A hazardous gas monitoring system, comprising:
a panel comprising a panel wall and a plurality of sensing lines disposed on and extending along the panel wall, wherein each sensing line is configured to receive and monitor an air sample and each sensing line of the plurality of sensing lines comprises:
  a water separator to remove condensed moisture from the air sample;
  a coalescing filter disposed downstream of the water separator; and
  a flow and gas monitoring system disposed downstream of the coalescing filter, wherein the water separator, the coalescing filter, and the flow and gas monitoring system are disposed on the panel wall, and wherein the flow and gas monitoring system comprises a flow indicator configured to provide a direct visual indication of a sample flow of the air sample flowing in a respective sensing line and a gas sensor configured to detect a presence of a hazardous gas in the sample flow.

2. The hazardous gas monitoring system of claim 1, wherein each sensing line of the plurality of sensing lines splits into a flow and gas monitoring line and a drainage line.

3. The hazardous gas monitoring system of claim 2, wherein the split between the flow and gas monitoring line and the drainage line occurs at the coalescing filter.

4. The hazardous gas monitoring system of claim 2, wherein, in each sensing line of the plurality of sensing lines, a first flow limiting orifice is disposed along the flow and gas monitoring line downstream of both the flow indicator and the gas sensor of the flow and gas monitoring system to limit sample flow, and a second flow limiting orifice is disposed along the drainage line to limit drainage flow.

5. The hazardous gas monitoring system of claim 1, wherein respective water separators of at least two sensing lines of the plurality of sensing lines are coupled to a common drainage line.

6. The hazardous gas monitoring system of claim 5, wherein, for the at least two sensing lines of the plurality of sensing lines, a respective flow limiting orifice is disposed between the respective water separator and the common drainage line.

7. The hazardous gas monitoring system of claim 5, wherein the common drainage line is coupled to a first ejector to discharge drainage flow to atmosphere.

8. The hazardous gas monitoring system of claim 7, wherein the at least two sensing lines of the plurality of sensing lines are coupled to a second ejector to discharge sample flow to the atmosphere.

9. The hazardous gas monitoring system of claim 8, wherein an instrument air supply is fluidly coupled to both the first and second ejectors to facilitate discharge.

10. The hazardous gas monitoring system of claim 1, wherein the hazardous gas monitoring system is configured to utilize a first sensing line of the plurality of sensing lines while a second sensing line of the plurality of sensing lines is deactivated or disconnected.

11. The hazardous gas monitoring system of claim 1, wherein the flow and gas monitoring system comprises a flow monitor configured to detect a parameter of the air sample in a respective sensing line and to determine if the parameter is at an undesired level.

12. The hazardous gas monitoring system of claim 1, wherein the panel is disposed within a cabinet, and wherein the cabinet comprises a heater configured to keep water from freezing within the plurality of sensing lines on the panel.

13. The hazardous gas monitoring system of claim 1, comprising heat traces disposed on portions of the sensing lines outside the panel to heat the sensing lines to keep water from freezing within the sensing lines.

14. The hazardous gas monitoring system of claim 1, wherein the plurality of sensing lines is coupled to an enclosure, and the air sample is from air within the enclosure.

15. The hazardous gas monitoring system of claim 1, wherein the plurality of sensing lines is coupled to a plurality of enclosures, and the air samples are from air within the plurality of enclosures.

16. A hazardous gas monitoring system, comprising:
a panel comprising a panel wall and a plurality of sensing lines disposed on and extending along the panel wall, wherein each sensing line is configured to receive and monitor an air sample from an enclosure housing a turbomachine, and each sensing line of the plurality of sensing lines comprises a water separator disposed on the panel wall to remove condensed moisture, and the plurality of sensing lines discharge respective air samples to the atmosphere.

17. The hazardous gas monitoring system of claim 16, wherein the plurality of sensing lines discharges the respective air samples to atmosphere via a plurality of ejectors.

18. The hazardous gas monitoring system of claim 17, wherein the plurality of ejectors comprises a first ejector coupled to at least a first sensing line and a second sensing line of the plurality of sensing lines and a second ejector coupled to a common drainage line coupled to respective water separators of the plurality of sensing lines.

19. A hazardous gas monitoring system, comprising:
a panel comprising a panel wall and a first sensing line and a second sensing line both disposed on and extending along the panel wall, wherein the first and second sensing lines are each configured to receive and monitor an air sample from an enclosure housing a turbomachine, and the first and second sensing lines each comprise a water separator disposed on the panel wall to remove condensed moisture, wherein a respective water separator of the first and second sensing lines are coupled to a common drainage line disposed on the panel wall, and a respective flow limiting orifice disposed on the panel wall is disposed between the respective water separator and the common drainage line.

* * * * *